(12) United States Patent
Vashist et al.

(10) Patent No.: US 10,344,100 B1
(45) Date of Patent: Jul. 9, 2019

(54) MICRO/NANO MAGNETIC HYDROGELS WITH AUTOFLUORESCENCE FOR THERAPEUTIC AND DIAGNOSTIC APPLICATIONS

(71) Applicants: Arti Vashist, Miami, FL (US); Ajeet Kaushik, Doral, FL (US); Madhavan Nair, Coral Gables, FL (US)

(72) Inventors: Arti Vashist, Miami, FL (US); Ajeet Kaushik, Doral, FL (US); Madhavan Nair, Coral Gables, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/907,703

(22) Filed: Feb. 28, 2018

(51) Int. Cl.
| | |
|---|---|
| *C08B 37/08* | (2006.01) |
| *A61K 49/18* | (2006.01) |
| *A61K 49/00* | (2006.01) |
| *G01N 33/543* | (2006.01) |
| *A61K 47/61* | (2017.01) |
| *A61K 31/675* | (2006.01) |
| *A61K 49/12* | (2006.01) |

(52) U.S. Cl.
CPC .......... *C08B 37/003* (2013.01); *A61K 31/675* (2013.01); *A61K 47/61* (2017.08); *A61K 49/0093* (2013.01); *A61K 49/126* (2013.01); *A61K 49/1824* (2013.01); *G01N 33/54346* (2013.01)

(58) Field of Classification Search
None
See application file for complete search history.

(56) References Cited

U.S. PATENT DOCUMENTS

2014/0286872 A1* 9/2014 Zhang ............... G01N 33/5091 424/9.3

FOREIGN PATENT DOCUMENTS

WO WO-2017177265 A1 * 10/2017 ............. A61K 38/09

OTHER PUBLICATIONS

Junise et al (Journal of Pharmaceutical Technology, Research and Management. vol. 2, No. 2, Nov. 2014 pp. 159-170).*
Khanmohammadi et al (Investigation of Size and Morphology of Chitosan Nanoparticles Used in Drug Delivery System Employing Chemometric Technique. Iran J Pharm Res. 2015 Summer; 14(3): 665-675).*
Wikipedia (https://en.wikipedia.org/wiki/Castor_oil (downloaded on Oct. 19, 2018). (Year: 2018).*
Vashist et al (Interpenetrating biopolymer network based hydrogels for an effective drug delivery system. Carbohydrate Polymers. vol. 87, Issue 2, Jan. 15, 2012, pp. 1433-1439) (Year: 2012).*
Ding, H. et al., "Enhanced blood-brain barrier transmigration using a novel transferrin embedded fluorescent magneto-liposome nanoformulation," *Nanotechnology*, 2014, pp. 055101 (14pp), vol. 25.
Sharmin, E. et al., Synthesis, characterization, antibacterial and corrosion protective properties of epoxies, epoxy-polyols and epoxy-polyurethane coatings from linseed and *Pongamia glabra* seed oils, *International Journal of Biological Macromolecules*, 2007, pp. 407-422, vol. 40.

* cited by examiner

*Primary Examiner* — Jake M Vu
(74) *Attorney, Agent, or Firm* — Saliwanchik, Lloyd & Eisenschenk

(57) ABSTRACT

Hydrogel nanoparticles and microparticles are prepared by a water-in-oil method from natural polymers that are water miscible, a hydrophobic polyol and a crosslinking agent. The hydrogel nanoparticles are auto fluorescent and can be used for imaging of cells and a biological entity. The hydrogel nanoparticles and microparticles can include magnetic nanoparticles and carry desired bioactive entities. The hydrogel nanoparticles and microparticles are useful for diagnostics and as therapeutics purposes including drug delivery, imaging of drug migration, and selectivity by the tagging or binding of the hydrogel nanoparticles and microparticles with appropriate antibodies or antigens.

17 Claims, 16 Drawing Sheets

MICRO/NANO MAGNETIC HYDROGELS WITH AUTOFLUORESCENCE FOR THERAPEUTIC AND DIAGNOSTIC APPLICATIONS

This invention was made with government support under DA040537 awarded by the National Institutes of Health and DA037838 awarded by the National Institutes of Health. The government has certain rights in the invention.

BACKGROUND OF INVENTION

Hydrogels are the three-dimensional network of hydrophilic polymers which have the ability to imbibe large amount of water inside them. Their soft porous structure makes them resemble the human tissue and serves as prefect candidate to be used in drug delivery and tissue engineering applications. Hydrogels can be designed and developed in various forms such as films, crystals and particles for drug delivery application. Recent studies showed that the nanoscale size range hydrogel particles are of utmost importance in therapeutics and diagnostics and thus research on the microgels and nanogels particles gain significant attention. Both microgels and nanogels particles show improved prospective in imaging, therapeutics delivery and tissue engineering.

BRIEF SUMMARY

Embodiments of the invention are directed to hydrogel nanoparticles or microparticles that are cross-linked gels of at least one water miscible polymer derived from natural sources, at least one hydrophobic polyol, and a crosslinking agent, wherein the hydrogel nanoparticle has a spherical shape, the nanoparticle or microparticle is from 40 nm to 500 μm in cross-section, and the nanoparticle is auto fluorescent. The water miscible polymer can be, but is not limited to, chitosan, hydroxyethyl cellulose, hydroxypropyl cellulose, hydroxyl methyl cellulose, methyl cellulose, or a combination thereof. The hydrophobic polyol can be, but is not limited to, linseed oil. The cross-linking agent can be, but is not limited to, glutaraldehyde. The hydrogel nanoparticles or microparticles can further comprise magnetic nanoparticles. The magnetic particle can be, but is not limited to, ferric oxide. The hydrogel nanoparticles or microparticles can further comprise a drug. The hydrogel nanoparticles or microparticles can be aggregated or isolated. The hydrogel nanoparticles or microparticles can be tagged with an antigen or an antibody.

In an embodiment of the invention, an imaging particle comprises the hydrogel nanoparticles or microparticle. The imaging particle can be magnetic, and can further comprise a drug, an antigen, or an antibody.

Another embodiment of the invention is directed to a method of preparing a hydrogel nanoparticles or microparticles described above, where at least one water miscible polymer derived from natural sources and at least one hydrophobic polyol are combining at least one water miscible polymer in a water-in-oil emulsion comprising a paraffin oil, water, and an emulsifying agent wherein water is suspended in a continuous phase of paraffin oil. A cross-linking agent and at least one hydrophobic polyol are added to the water-in-oil emulsion, where upon stirring the water-in-oil emulsion forms the hydrogel nanoparticles. The paraffin oil can be heavy liquid paraffin oil. The emulsifying agent can be Tween 80. The crosslinking agent can be glutaraldehyde. In an embodiment of the invention the method can include adding a magnetic nanoparticle, such as ferric oxide. In another embodiment of the invention a drug can be added to the nanoparticle or microparticle formulation.

DETAILED DISCLOSURE

Figure 1:
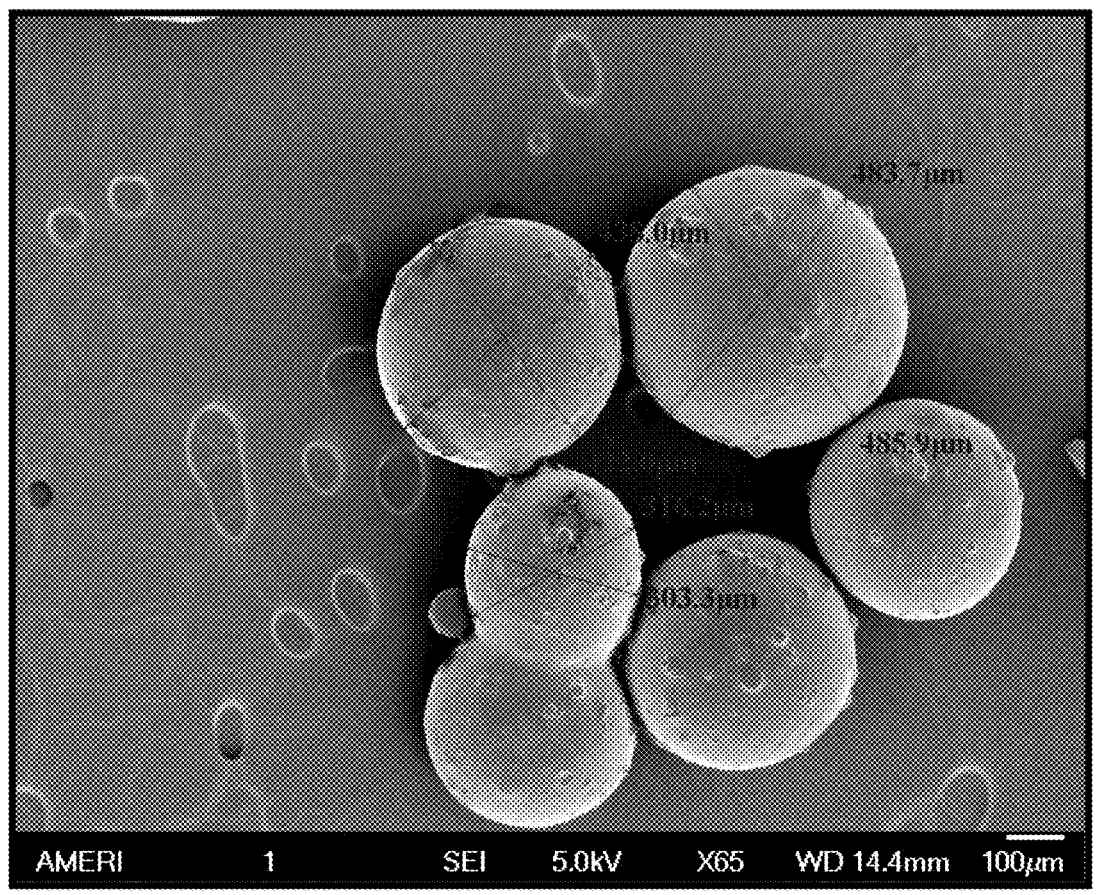
FIG. 1 shows a scanning electron micrograph (SEM) image of hydrogel microparticles, according to an embodiment of the invention.

Embodiments of the invention are directed to hydrogel nanoparticles and microparticles (hydrogel nanoparticles) that are high dispersible in aqueous medium as biocompatible encapsulates where the drug retains its integrity in the developed hydrogel nanoparticle matrix. The developed hydrogel nanoparticles exhibit fluorescence. The hydrogel nanoparticles increase the bioavailability of the drug by protecting it in the systemic circulation and enhance the drug's retention time. The hydrogel nanoparticle comprises one or more natural based polymers and has application for image guided therapy in addition to their use for drug delivery. These hydrogel nanoparticles have sizes that extend to a few micrometers, and for purposes of the invention that termed hydrogel nanoparticles may extend into the size range typically referred to as hydrogel microparticles. These hydrogel nanoparticles can be formed or derived from biopolymers, such as, but not limited to, chitosan, hydroxyethyl cellulose (HEC), hydroxylpropylcellulose (HPC), carboxymethyl cellulose (CMC), methyl cellulose (MC), starches, and pectin and can include magnetic nanoparticles (MNP) for example, iron oxide (III) nanoparticles using water-in-oil emulsion polymerization techniques. Copolymers of sodium alginate and acrylamide can be combined with chitosan and magnetic nanoparticles to form the hydrogel nanoparticles. Hydrogel nanoparticles with iron oxide (III) exploit the magnetic character for targeted drug delivery in a patient. Elements of hydrophobicity to enhance the stability of hydrogel nanoparticles can be achieved by the addition of linseed oil based polyol or other hydrophobic polyols, such as other vegetable based polyols, including, but not limited to, ricinoleic acid, lesquerollic acid, strophantus, coriaria, cardamine impatiens, sebastiana commersoniana and capparis zeylanica. The inclusion of the polyol results in formation of an interpenetrating network (IPNs) and in this form an increased drug loading capacity and hydrogel stability is achieved. The hydrogel nanoparticles are crosslinked gels in the form of spheres. Drug binding readily confirmed using (Fourier-transform infrared spectroscopy) FT-IR, SEM, and TEM methods. The biocompatibility of the hydrogel nanoparticle is readily observed by XTT analysis in PBMCs and Microglia cells. The hydrogel nanoparticles are non-toxic to host cells.

In an embodiment of the invention, hydrogel nanoparticles are synthesized with natural polymers. In an exemplary embodiment, hydroxyethyl cellulose, chitosan and linseed oil based polyol form hydrogel microparticles and hydrogel nanoparticles in an oil emulsion. Various formulations with anti-retroviral drug and without the drug containing magnetic nanoparticles (MNP) have been fabricated. In an exemplary embodiment of the invention, tenovofir disoproxil (TNF) was incorporated into the hydrogel nanoparticles and studied for in vitro drug loading and release kinetics. The pre-gelled composition of various exemplary formulations is summarized in Table 1, below.

TABLE 1

Exemplary hydrogel nanoparticle compositions

| Sample Code | Chitosan (g) | Hydroxyethyl cellulose (g) | Glutaraldehyde (mL) | Polyol (2%) | TNF (mg) | MNP (µL) |
| --- | --- | --- | --- | --- | --- | --- |
| TCH-1 | 0.7 | 0.3 | 5.0 | 1.0 | 20 | 0 |
| TCH-2 | 0.7 | 0.3 | 5.0 | 1.0 | 20 | 500 |
| TCH-3 | 0.7 | 0.3 | 5.0 | 1.0 | 0 | 500 |
| TCH-4 | 0.7 | 0.3 | 5.0 | 1.0 | 0 | 0 |

The unexpected autofluorescence and inclusion of components for magnetic behavior allows a drug delivery formulation to possess target specificity combined with in vivo drug monitoring. The system may be used where these hydrogel nanoparticles are tagged, either chemically or physically, with antigen/antibody for specificity for a disease of interest. Hydrogel nanoparticles can be used for drug formulations that targeted delivery of active drug molecules. Autofluorescence allows in vivo imaging based diagnostic vehicles with these hydrogel nanoparticles. Flow cytometery results indicate that these hydrogel nanoparticles undergo uptake by cells, such as PBMCs and CHME5, and are useful for cell mediated drug delivery.

The nanoparticles, according to embodiments of the invention have been tested in T-2 and T-4 formulation for their efficiency to cross the blood brain barrier (BBB) in an in vitro BBB model, using the reported BBB model disclosed in Nair et al., *Nanotechnology* 2014, 25, 055101.

Methods and Materials

Materials

Chitosan (CH) (448869-50G, Sigma Aldrich), hydroxyethyl cellulose (HEC) (TCI, 200-300 mPa·s, 2% in water), heavy liquid paraffin oil (ACROS Organics), Tween 80 (Sigma Aldrich), Linseed Oil (Sigma Aldrich, fp 113° C. d 0.93 g/ml at 25° C.), n-Hexane (Merck, India), Glycine (Mwt. 75.07 g/mol: Density 1.607 $g/cm^3$), glacial acetic acid, hydrogen peroxide, (Sigma Aldrich) were used as received. Tenovofir disoproxil fumerate (USP-1643656) was used as the model drug. Linseed oil polyol was prepared as disclosed in Sharmin et al., *International Journal of Biological Macromolecules,* 2007, 40, 407-22.

Preparation of the Hydrogel Microparticles and Nanoparticles

Figure 2:
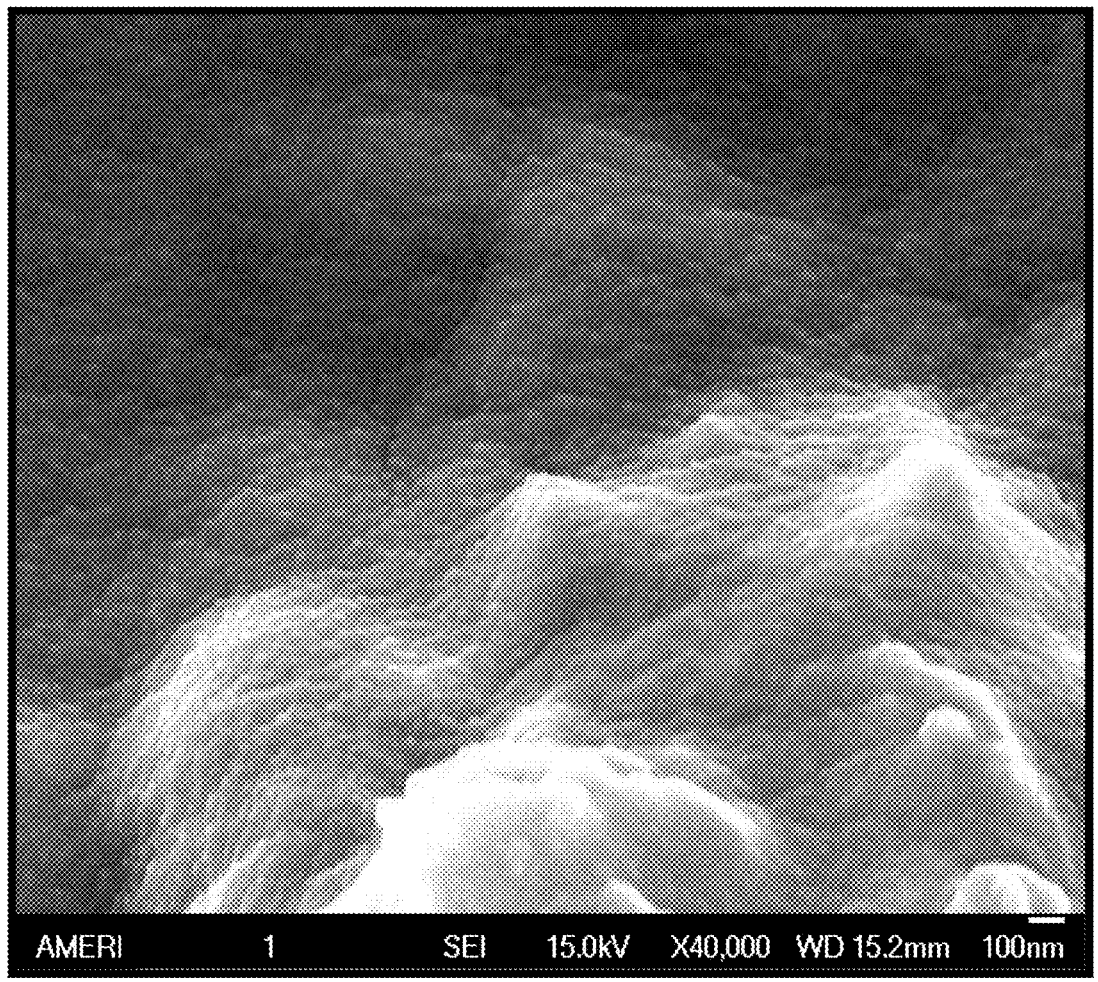
FIG. 2 shows a SEM image of powdered hydrogel nanoparticles, according to an embodiment of the invention.
Figure 3:
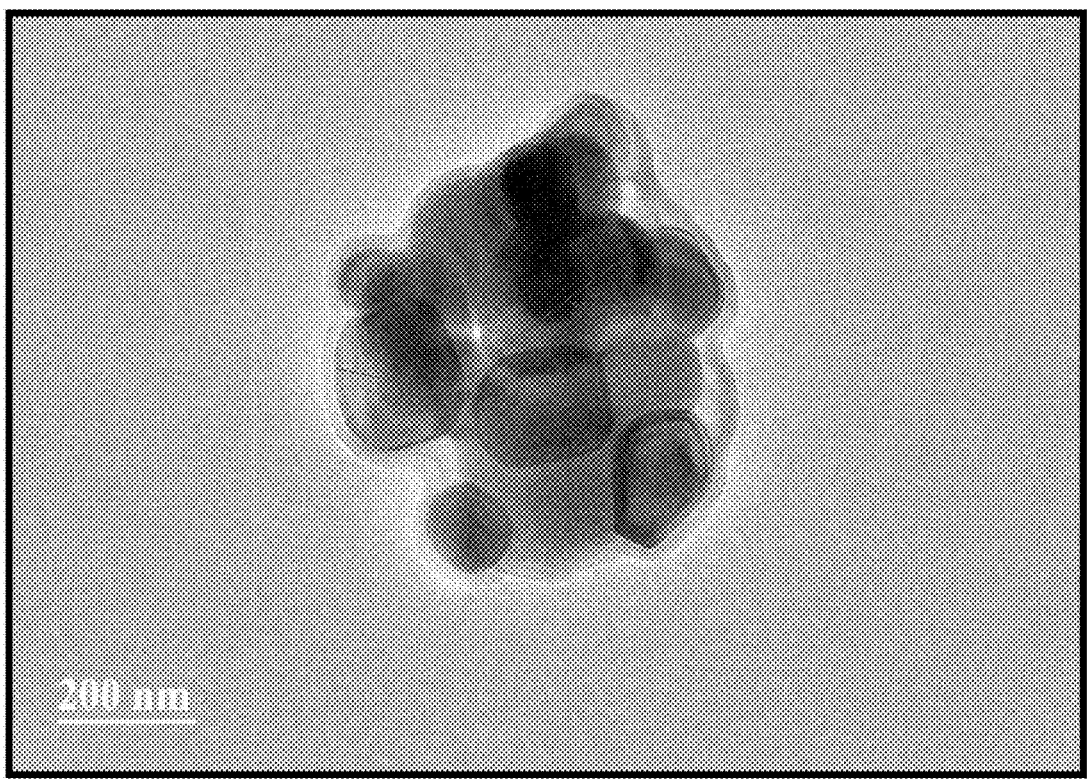
FIG. 3 shows a transmission electron microscope (TEM) image of aggregated hydrogel nanoparticles, according to an embodiment of the invention.
Figure 4:
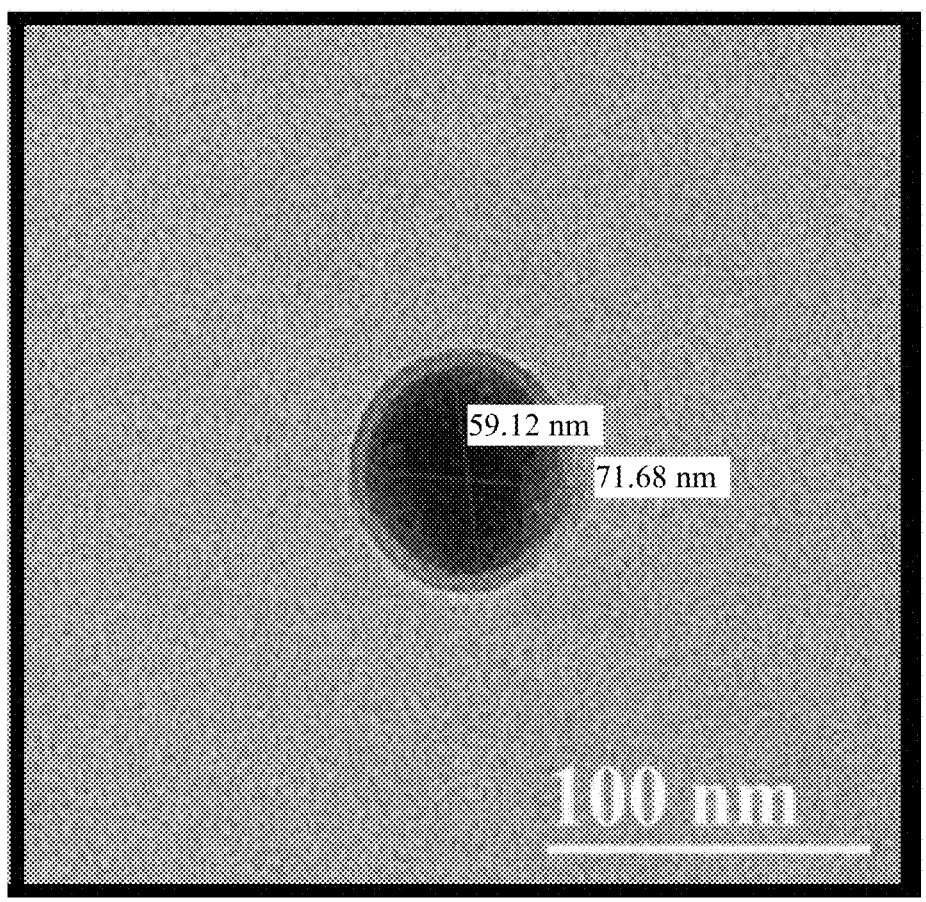
FIG. 4 shows a transmission electron microscope (TEM) image of a sorted hydrogel nanoparticle, according to an embodiment of the invention.
Figure 5A:
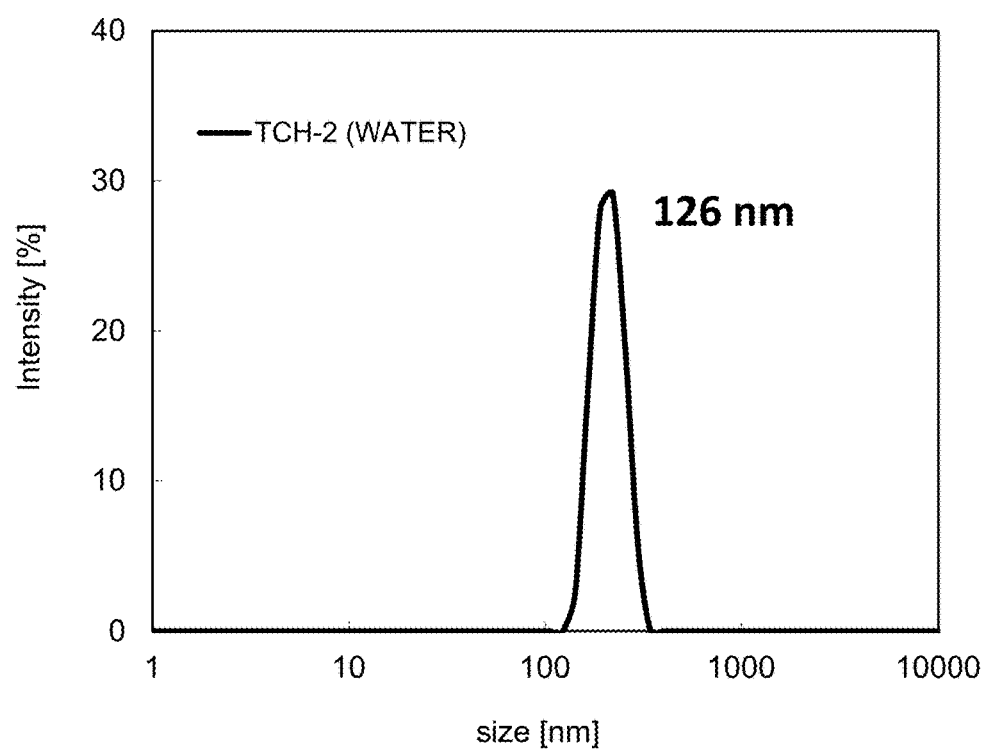
FIG. 5A shows a plot of the hydrodynamic diameter of a hydrogel nanoparticle in water, according to an embodiment of the invention.
Figure 5B:
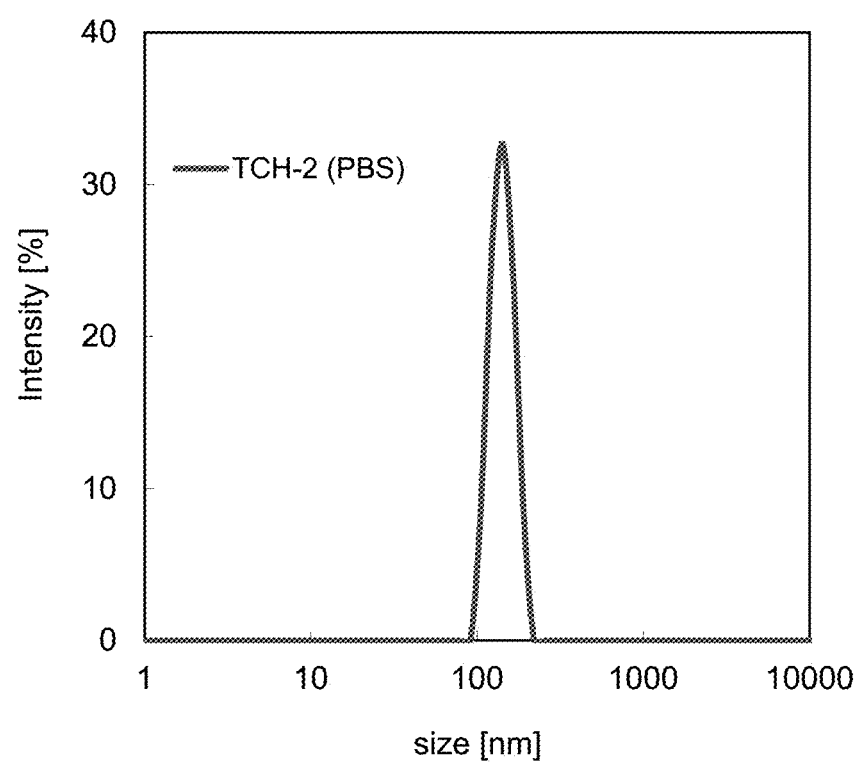
FIG. 5B shows a plot of the hydrodynamic diameter of a hydrogel nanoparticle in phosphate-buffered saline (PBS) solution, according to an embodiment of the invention.

Hydrogel nanoparticles of chitosan and hydroxyethyl cellulose (HEC) were prepared using a water-in-oil emulsion polymerization method. Linseed oil based polyol was used as a hydrophobic modifier. Polymer solution (20 ml of 2% (w/v)) was prepared by using chitosan and hydroxyethyl cellulose in 1% (v/v) acetic acid. Different formulations were prepared using medium molecular weight and low molecular weight chitosan. Magnetic nanoparticles (MNP) of $Fe_2O_3$ were prepared using a co-precipitation method as disclosed in Ding et al., *Nanotechnology,* 2014, 25, 055101. The synthesized MNP were added to the polymer solution and blended for 30 mins. The drug tenofovir disoproxil fumarate was added (w/w) in polymer solution and stirred for 10 mins. A separate beaker was used to make a mixture of liquid paraffin oil and 1% (w/w) Tween 80. The polymer solution was added dropwise to the mixture of oil and surfactant with a stirring rate of 1400 rpm on a magnetic stirrer. The mixing of the solution was continued for 20 minutes followed by the addition of glutaraldehyde (5 ml) for another 10 minutes. The linseed oil polyol was added to the reaction mixture and stirring was continued at 1400 rpm for 5 hours. The particles were washed thoroughly with n-hexane to remove excess oil. Any excess glutaraldehyde was deactivated by 0.1 M glycine. The washed hydrogel particles were dried at room temperature. A scanning electron microscope (SEM) image of the magnetic microparticles is shown in FIG. 1. The powder hydrogel microparticles (hydrogel nanoparticles) are shown in the SEM of FIG. 2. A TEM of aggregated clump of hydrogel nanoparticles is shown in FIG. 3 and an isolated sorted particle is shown in FIG. 4. The hydrodynamic dimensions of the hydrogel nanoparticles are plotted in FIGS. 5A and 5B for hydrogel nanoparticles in water and PBS.

Figure 6A:
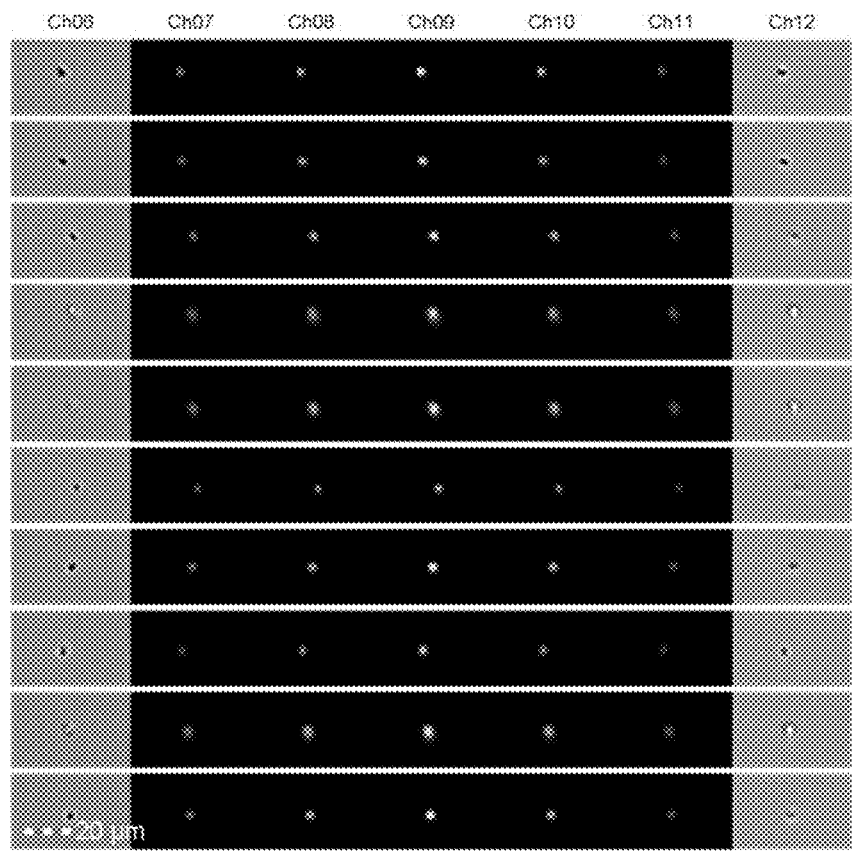
FIG. 6A shows representative images of single particles of the hydrogel nanoparticles, according to an embodiment of the invention.
Figure 6B:
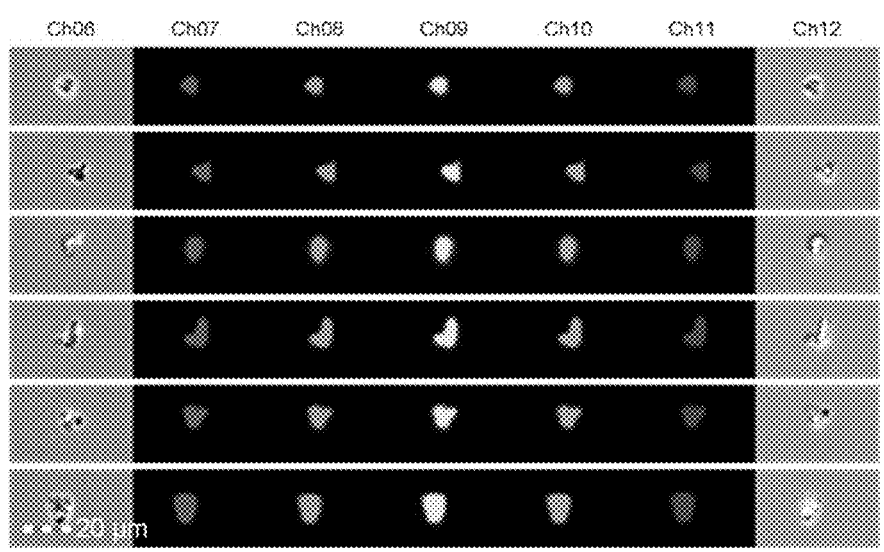
FIG. 6B shows representative images of aggregate clumps of the hydrogel nanoparticles, according to an embodiment of the invention.
Figure 7:
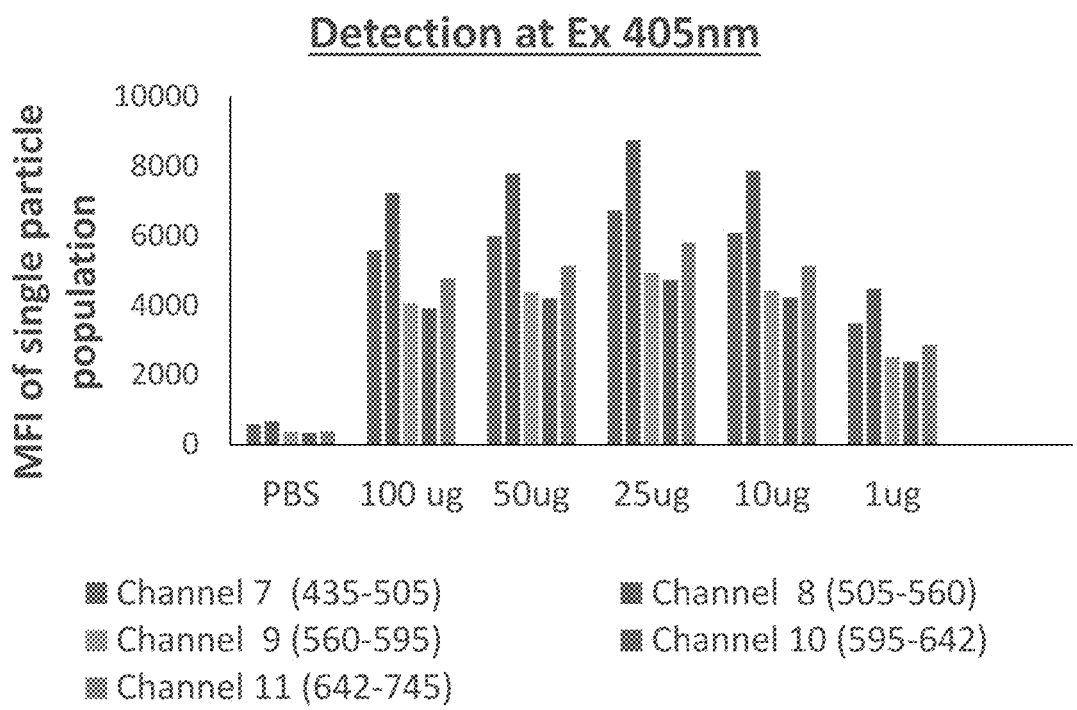
FIG. 7 shows a bar graph of the mean intensity values of the single particle population for each channel of a hydrogel nanoparticle with the bars for a given channel in numerical order from left to right, according to an embodiment of the invention.

Images were acquired from different concentrations of hydrogel nanoparticles (1-100 µg/mL) to get an emission spectrum of the hydrogel nanoparticle particles at 405 nm excitation to check the presence of fluorescence. Bright field channels 6 and 12 were assigned. FIGS. 6A and 6B show representative images of single particles and aggregate clumps of the hydrogel nanoparticles, respectively Post-acquisition, during analysis, based on population size, single particle population and clumps were sieved. The mean intensity of each channel or detection bandwidth was calculated. The graph of FIG. 7 shows the mean intensity values of the single particle population for each channel, where emission in channel 8 (505-560 nm) shows the maximum intensity for each concentration while 25 µg/ml concentration shows the maximum intensity.

The reduction in intensity in further dilutions may be due to less availability of single particles as the materials were more diluted. As dilutions were increased, image acquisition time increased to acquire the same number of images from each sample.

Figure 8A:
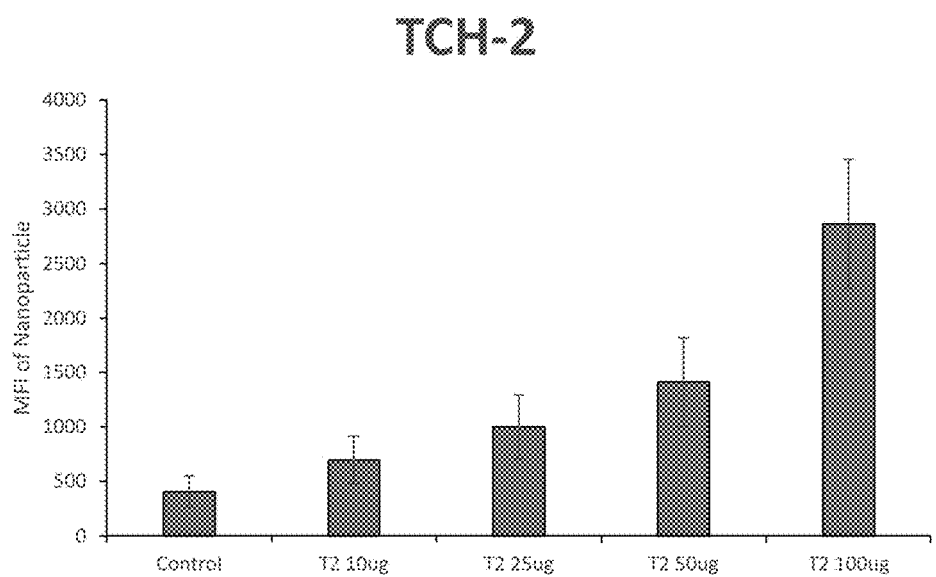
FIG. 8A shows a plot of the mean fluorescence intensity for the uptake of TCH-2 in peripheral blood mononuclear cells (PBMCs), according to an embodiment of the invention.
Figure 8B:
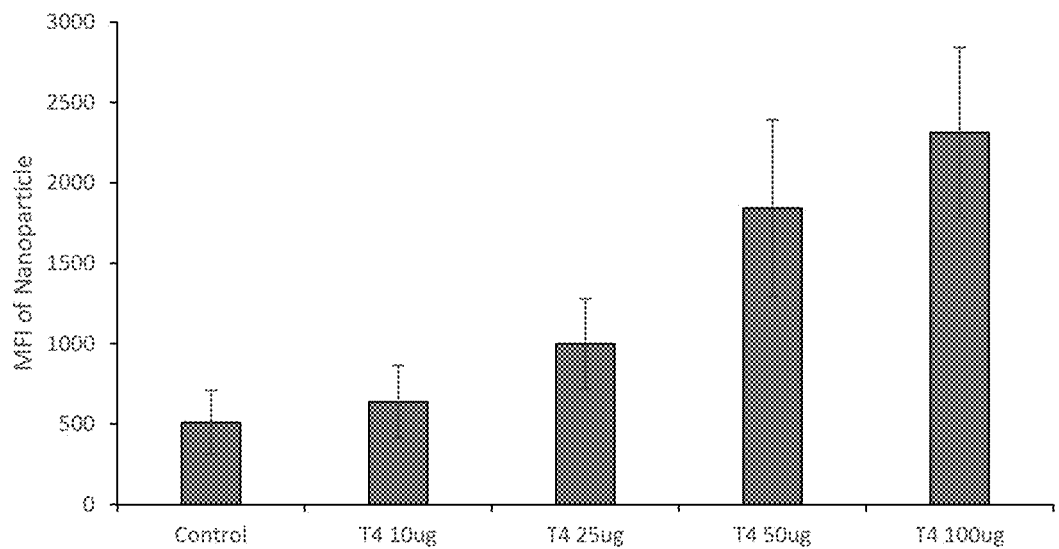
FIG. 8B shows a plot of the mean fluorescence intensity for the uptake of TCH-4 in PBMCs, according to an embodiment of the invention.
Figure 9A:
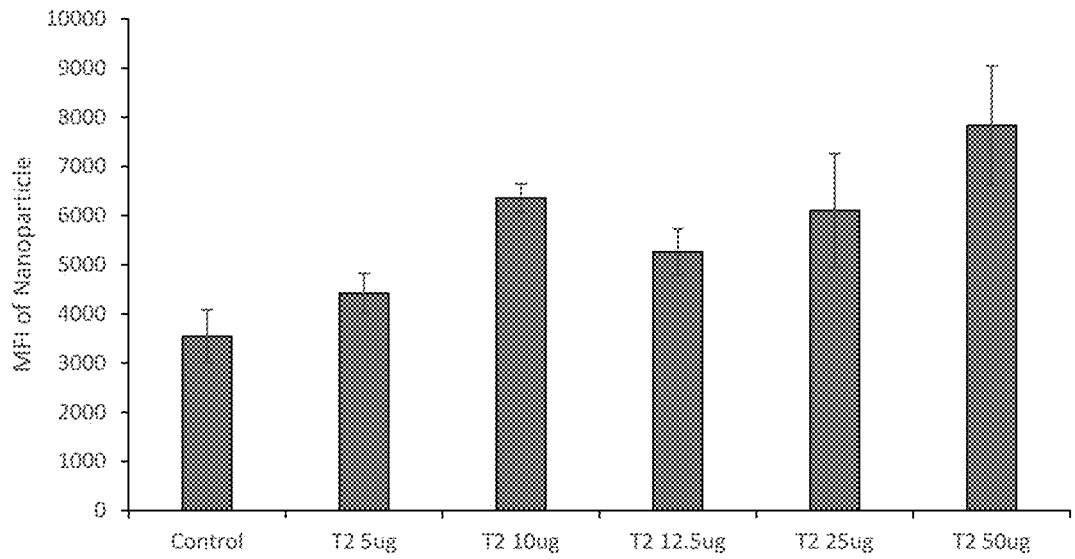
FIG. 9A shows a plot of the mean fluorescence intensity for the uptake of TCH-2 in CMHE5 cells, according to an embodiment of the invention.
Figure 9B:
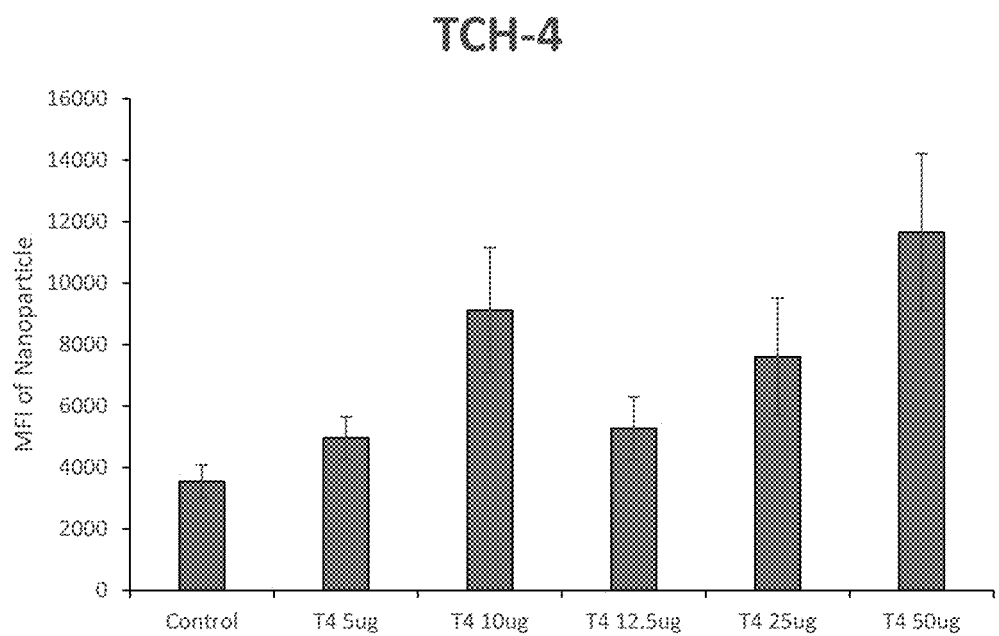
FIG. 9B shows a plot of the mean fluorescence intensity for the uptake of TCH-4 in CMHE5 cells, according to an embodiment of the invention.

Following channel selection, hydrogel nanoparticles of various concentrations were incubated with cells (PBMCs and CMHE5) and the cells were harvested, washed, 7-aminoactinomycin D (7-AAD) was added, and images were acquired using FlowSight® Imaging Flow Cytometer. Because of multichannel fluorescence of the hydrogel nanoparticles, for analysis, combination of the hydrogel nanoparticles with other dyes, such as, Amnis FlowSight®, was not done because compensation was not possible. The hydrogel nanoparticles were analyzed without compensation at predetermined channel 08. Based on intensity of channel 8, and assisted by single cell images, the cell's up-take of the hydrogel nanoparticles was examined in a concentration dependent manner. Using 100 µg/ml of hydrogel nanoparticle, a significant Hydrogel nanoparticle uptake of PBMCs was observed for TCH-2 and TCH-4 hydrogel nanoparticle formulations, as indicated in FIGS. 8A and 8B. Similarly, for CMHE5 cells, a significant uptake of hydrogel nanoparticle at a 50 µg concentration was observed for TCH-2 and TCH-4, as indicated in FIGS. 9A and 9B. Fluorescence was confirmed through flow cytometry by adjusting the excitation and emission wavelength, with excitation and emission at 405 nm and 505-560 nm respectively.

Figure 10A:
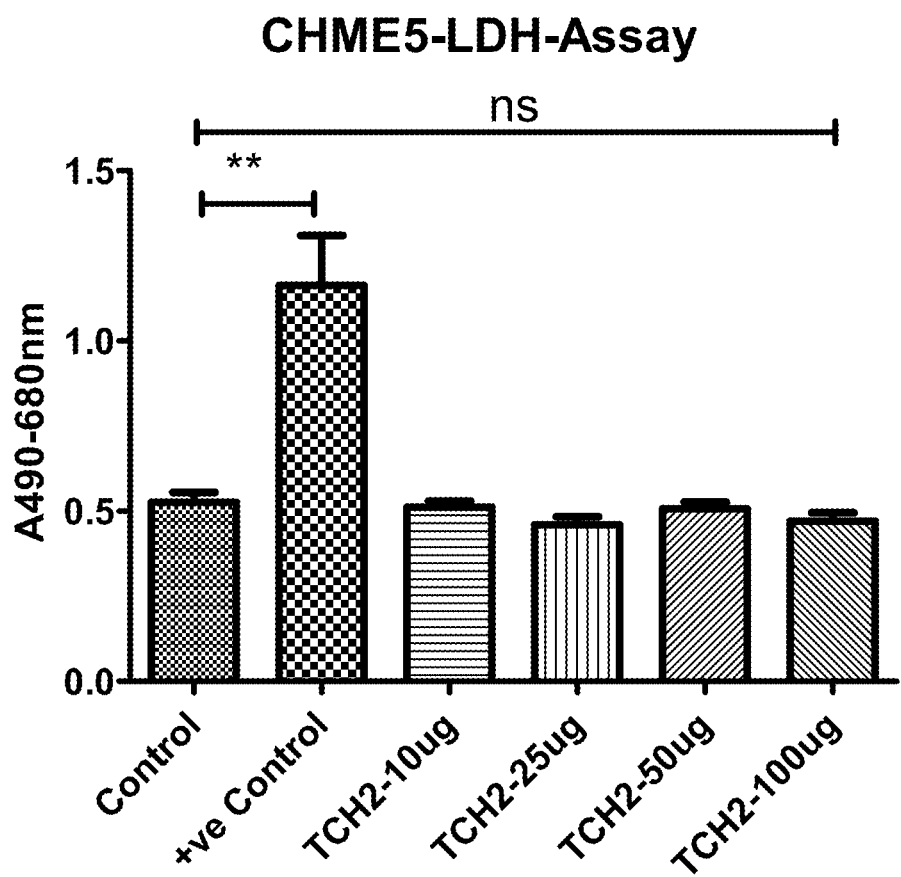
FIG. 10A shows a bar chart for the Lactate Dehydrogenase (LDH) cytotoxicity of TCH-2 in CMHE5 cells, according to an embodiment of the invention.
Figure 10B:
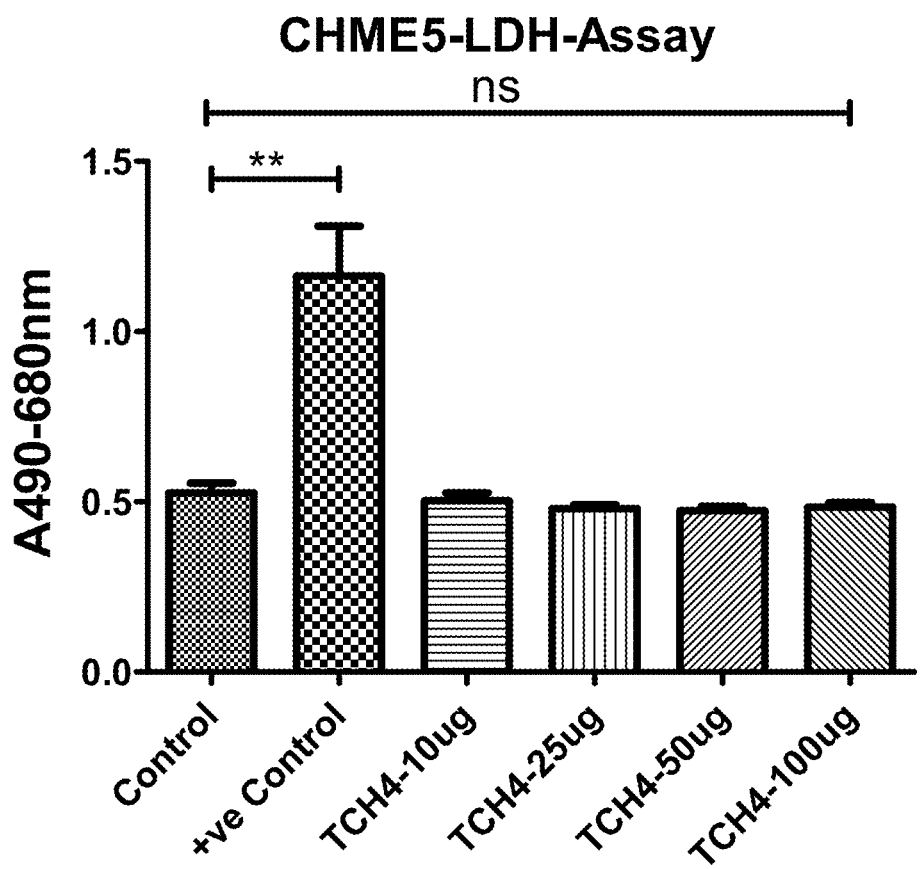
FIG. 10B shows a bar chart for the Lactate Dehydrogenase (LDH) cytotoxicity of TCH-4 in CMHE5 cells, according to an embodiment of the invention.

CHME5 cells (10,000 cells per well) were plated in a 96-well plate in DMEM medium supplemented with 10% serum and pen-strep and incubated at 37° C. with 5% $CO_2$. After 24 hrs, various concentration hydrogel nanoparticle formulations (10-100 µg/ml) had TCH-2 and TCH-4 added to the culture media and incubated for 24 hrs. LDH cytotoxicity was measured using a Pierce LDH cytotoxicity assay kit. It was observed that both hydrogel nanoparticle formulation, TCH-2 and TCH-4 (10-100 µg/ml), are biocompatible showing no cytotoxicity, as indicated in FIGS. 10A and 10B.

Figure 11A:
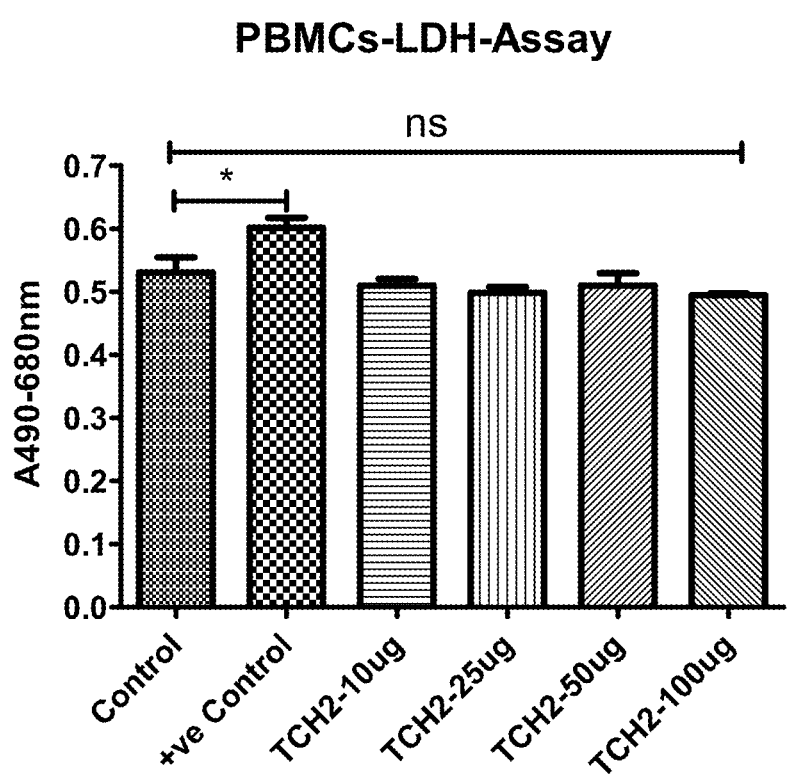
FIG. 11A shows a bar chart for the Lactate Dehydrogenase (LDH) cytotoxicity of TCH-2 in PBMCs, according to an embodiment of the invention.
Figure 11B:
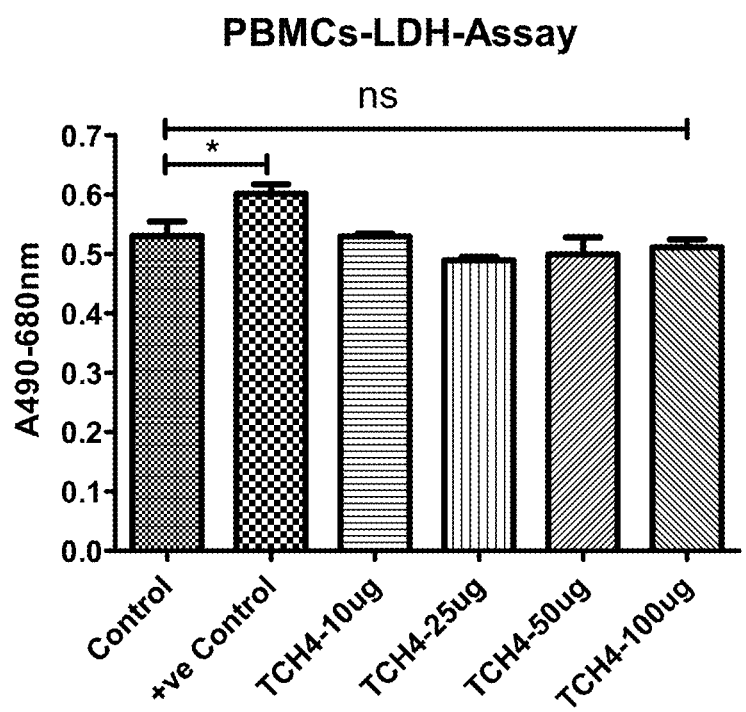
FIG. 11B shows a bar chart for the Lactate Dehydrogenase (LDH) cytotoxicity of TCH-4 in PBMCs, according to an embodiment of the invention.

PBMCs (10,000 cells per well) were plated in a 96 well plate in RPMI medium supplemented with 10% serum and pen-strep and incubated at 37° C., 5% $CO_2$. After 24 hrs, various concentration hydrogel nanoparticle formulations (10-100 µg/ml) had TCH-2 and TCH-4 added to the culture media and incubated for 24 hrs LDH cytotoxicity was measured using a Pierce LDH cytotoxicity assay kit. It was observed that both hydrogel nanoparticle formulations TCH-2 and TCH-4 (10-100 µg/ml) are biocompatible showing no cytotoxicity, as indicated in FIGS. 11A and 11B.

The emission feature of the hydrogel nanoparticle allows detection of hydrogel nanoparticle with various instruments upon adjusting the excitation and emission wavelengths. The fluorescence can be observed using a plate reader, such as a Synergy HT multimode microplate reader (BioTek) upon adjusting the excitation and emission wavelengths to 590/20 and 645/40, respectively. The hydrogel nanoparticles constitute a unique imaging agent having a wide detection limit that is accessible for a variety of instruments and may be used for detection of the presence of various bioactive drugs by tagging or binding the drug to or within the hydrogel particles at the same time and reading through different channels. Hydrogel nanoparticle formulation (TCH-4), which does not contain any drug or magnetic nanoparticles, display auto fluorescence and biocompatibility for use as imaging agents for other bioactive molecules bound to or within the hydrogel nanoparticles.

Method for BBB:

In vitro BBB transmigration was examined in the presence or absence of an external magnetic force to observe transport of the synthesized hydrogel nanoparticles. Transmigration study for the hydrogel nanoparticles formulations was conducted in 24 hours after introduced to the BBB culture with membrane integrity confirmed by the TEER measurements. Known concentrations of the nanoparticles exhibiting fluorescence were added to the apical chamber and incubated at 37° C. in the presence or absence of a magnetic force of 0.08 T placed externally below the transwell's basolateral chamber. Samples were measured at wavelength 590/20 nm-645/40 nm (Ex/Em) by microplate reader (Synergy HT, multi-mode microplate reader, BioTek, Winooski, Vt., USA). The transport of the hydrogel nanoparticles was calculated from the equation as % Transport=(fluorescent intensity in basal chamber)/(fluorescent intensity in apical chamber)×100.

Figure 12:
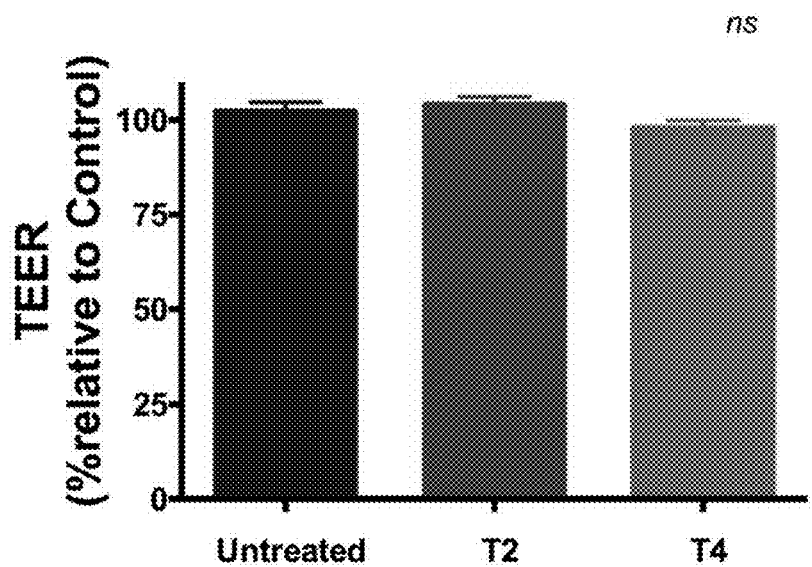
FIG. 12 shows a bar chart of the TEER of T2 and T4 hydrogel nanoparticles relative to untreated cells, according to an embodiment of the invention.
Figure 13:
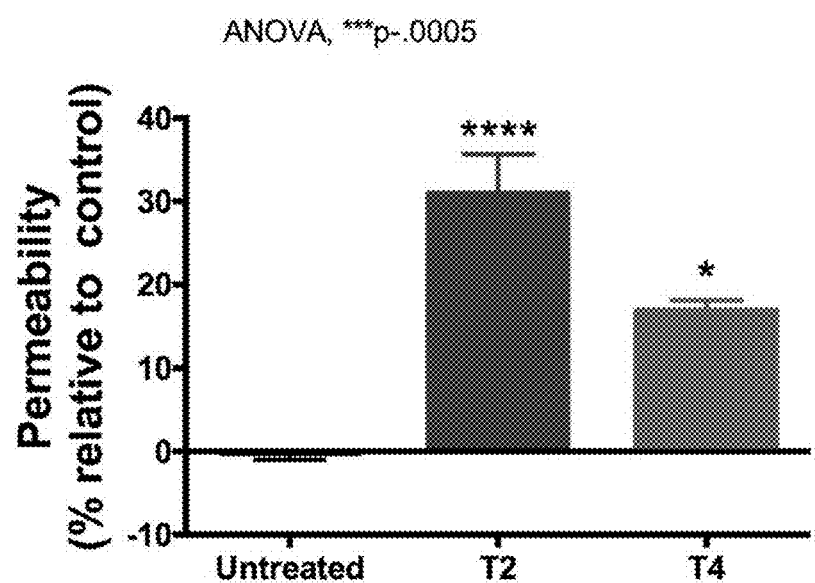
FIG. 13 shows a bar chart of the permeability across the BBB for T2 and T4 hydrogel nanoparticles relative to untreated cells, according to an embodiment of the invention.
Figure 14:
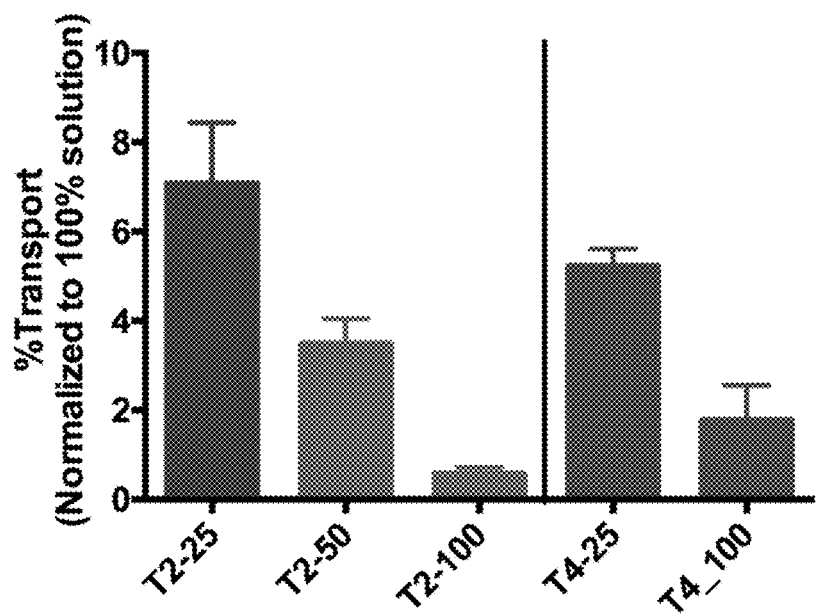
FIG. 14 shows a bar chart of the % transport across the BBB for T2 and T4 hydrogel nanoparticles, according to an embodiment of the invention.

The intrinsic characteristic of the hydrogel nanoparticles is their soft physical structure, which is advantageous for enhanced permeation across dynamic barriers present inside any cellular system of the human body. TEER results confirm that the integrity of the BBB was not affected by the addition of hydrogel nanoparticles, as shown in FIG. 12. The hydrogel nanoparticles (T2 and T4) showed increase d permeability in BBB Model, as shown in FIG. 13 Permeability results show that the T2 gel particles, which include of magnetic nanoparticles, show an increased permeability relative to T4, as shown in FIG. 13. The static magnetic force applied externally facilitates the permeability. In this manner an increase in permeability for T4 was significant. Moreover, Interestingly, T2 and T4 show transport, although less than 10%, across the BBB, including T4 nanoparticles that lacked magnetic particles as shown in FIG. 14.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. Hydrogel nanoparticles or microparticles, comprising a cross-linked gel of chitosan and hydroxyethyl cellulose and linseed oil polyol and a crosslinking agent, the nanoparticle or microparticle being auto fluorescent.

2. The hydrogel nanoparticles or microparticles according to claim 1, wherein the cross-linking agent is glutaraldehyde.

3. The hydrogel nanoparticles or microparticles according to claim 1, wherein the hydrogel nanoparticle or microparticle has a spherical shape.

4. The hydrogel nanoparticles or microparticles according to claim 1, wherein the hydrogel nanoparticle or microparticle is from 40 nm to 500 µm in cross-section.

5. The hydrogel nanoparticles or microparticles according to claim 1, further comprising magnetic nanoparticles.

6. The hydrogel nanoparticles or microparticles according to claim 5, wherein the magnetic nanoparticle is ferric oxide.

7. The hydrogel nanoparticles or microparticles according to claim 1, further comprising a drug.

8. The hydrogel nanoparticles or microparticles according to claim 1, wherein the hydrogel nanoparticles are aggregated or isolated.

9. The hydrogel nanoparticles or microparticles according to claim 1, wherein the hydrogel nanoparticles are tagged with an antigen or an antibody.

10. An imaging particle, comprising the hydrogel nanoparticles or microparticles according to claim 1.

11. The imaging particle according to claim 10, wherein the imaging particle is magnetic.

12. The imaging particle according to claim 10, further comprising a drug.

13. The imaging particle according to claim 10, further comprising an antigen or an antibody.

14. A method of preparing a hydrogel nanoparticles or microparticles according to claim 1, comprising:
providing chitosan and hydroxyethyl cellulose;
providing linseed oil polyol;
combining the at least one water miscible polymer in a water-in-oil emulsion comprising a paraffin oil, water, and an emulsifying agent wherein water is suspended in a continuous phase of paraffin oil;
adding a crosslinking agent to the a water-in-oil emulsion;
adding the linseed oil polyol to the water-in-oil emulsion; and
stirring the water-in-oil emulsion to form the hydrogel nanoparticles.

15. The method according to claim 14, wherein the paraffin oil is a heavy liquid paraffin oil, the emulsifying agent is Tween 80, and the crosslinking agent is glutaraldehyde.

16. The method according to claim 14, further comprising adding a magnetic nanoparticle.

17. The method according to claim 14, further comprising adding a drug.

* * * * *